April 6, 1965 F. M. SAKIYAMA Plant Pat. 2,490
AZALEA PLANT
Filed Jan. 9, 1964
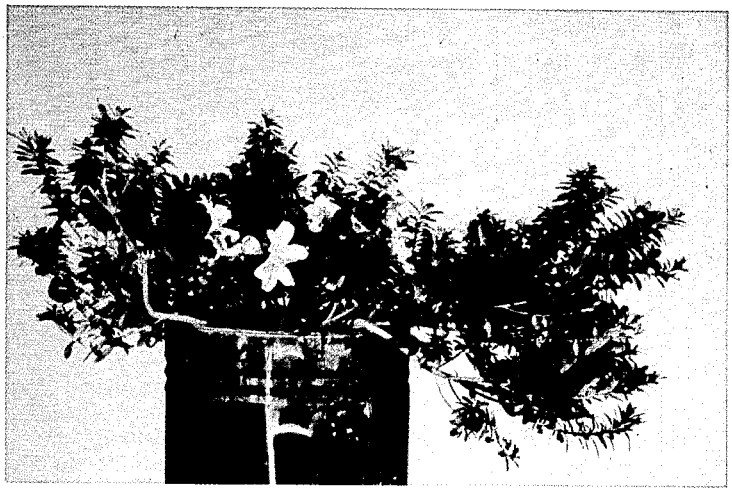
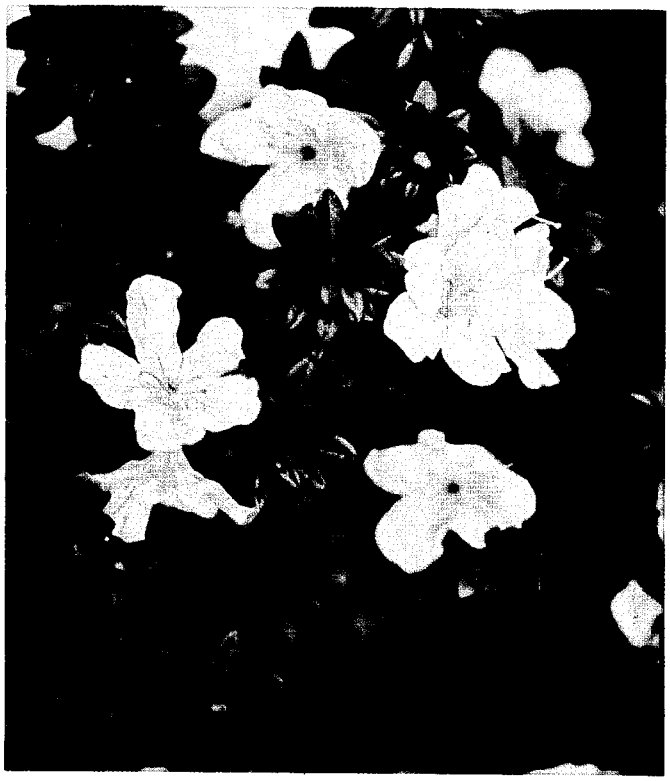
Inventor
F. M. Sakiyama
By: Robb & Robb
Attorneys.

United States Patent Office

Plant Pat. 2,490
Patented Apr. 6, 1965

2,490
AZALEA PLANT

Frank M. Sakiyama, 5006 N. Bartlett Ave.,
San Gabriel, Calif.

Filed Jan. 9, 1964, Ser. No. 336,847
1 Claim. (Cl. Plt.—56)

The present invention relates to a new and distinct variety of azalea plant which was discovered by me as a sport of a Southern Indica azalea known as "Duc de Rohan" (unpatented).

At the time of my discovery, referred to above, I was growing in my nursery a block of azaleas of the variety "Duc de Rohan." In the course of my care and cultivation of these plants, my attention was attracted to one plant which appeared to be substantially different from the variety "Duc de Rohan," as evidenced by a stunted or dwarfish habit of growth, and extremely small or miniature foilage. Upon closer examination of this unusual plant, I found that it apparently had developed as a sport of "Duc de Rohan," and I thereupon took immediate steps to separate this plant from the others and put it under careful observation. My further studies thereof disclosed that the foilage was darker in color than the parent variety and bloomed more profusely than the parent variety.

Continued tests and observations of the new sport, and of additional plants reproduced asexually therefrom by cuttings, as grown by me in my nursery at San Gabriel, California, and eleswhere under special tests, confirmed the distinctive characteristics of the originally discovered plant, as well as establshing other unique features which, taken altogether, convinced me was a new and unusual combination of characteristics which differentiate the new sport from its parent variety, as well as from all other azalea varieties of which I am aware, as evidenced by the following characteristics which are outstanding in the new sport:

(1) A natural dwarfish habit of growth which presents an aged appearance;

(2) Very small and abundant dark green leaves which more fully clothe the plant than the larger and more scattered leaves of the parent variety "Duc de Rohan";

(3) Profuse, colorful and silky pink flowers of attractive shape, said flowers being produced in greater abundance than the flowers of the parent variety;

(4) Good temperature tolerance, as evidenced by the fact that plants of the new sport have stood up well in temperatures ranging from as low as 25° F. to over 100° F.; and (5) A general attractiveness suitable for bonsai or sprawling type potted plantings, both with and without blooms, and without the need of any special care, with consequent special suitability for oriental type gardens, waterfall plantings and elsewhere, both in sunny locations, or in filtered shade.

The accompanying drawing shows a typical specimen plant of my new variety, as well as foliage and flower specimens on a somewhat enlarged scale, as depicted in color as nearly true as it is reasonably possible to make the same in a color illustration of this character.

The following is a detailed description of my new new azalea variety, with color terminology in accordance with Ridgway's Colour Standards and Nomenclature, except where general color terms of ordinary dictionary significance are obvious:

Locality where grown and observed: San Gabriel, California.

Propagation: Holds its distinguishing characteristics through succeeding propagations by cuttings.

Plant:

*Form.*—Dwarf; from about 14 to 20 inches tall at maturity when grown in the ground from cuttings, and from 11 to 14 inches tall when grown in containers.

*Habit.*—Stumpy; sprawly; appears and grows like an aged plant, with a natural bonsai appearance without requiring special attention.

Blooming habit: Profuse.

Blooming season: Midseason; suitable for forcing.

Foliage:

*Size.*—Small; average length about 1 inch, and average width about ⅜ inch.

*Quantity.*—Abundant.

*Color.*—New foilage: upper side—Parrot Green, Plate VI K; under side—Pale Yellow Green, Plate VI F. Old foliage: upper side—Cedar Green, Plate VI M; under side—Grass Green, Plate VI K.

*Shape.*—Oval pointed.

*Texture.*—Upper side—glossy. Underside—rough.

*Margin.*—Smooth edge.

*Disease resistance.*—Good, as evidenced by the fact that no disease problems have occurred over a period of several years, and no special attention has been required or given, as compared with other varieties grown under the same cultural conditions in the same locality at San Gabriel, California.

Flowers:

*Borne.*—Usually 3 to a stem.

*Quantity of bloom.*—Abundant, both outdoors and in greenhouse.

*Continuity.*—One season.

*Size.*—Average flower about 2 inches in diameter.

*Petalage.*—Number of petals under normal conditions—5. Color—Eosine Pink, Plate I D, with darker red blotch usually appearing on the base of at least the upper lobe of the corolla and sometimes extending slightly onto the adjacent lobes. Texture—silky. Appearance:—inside—pink color with dark rose dotted throat; outside—looks like crepe paper. Shape—bell shaped.

*General color tonality.*—Pink.

Bud: Color—dark rose like the throat and stamens.

Reproductive organs:

*Stamens.*—Color—Begonia Rose, Plate I D.

*Pollen.*—Color—Oxblood Red, Plate I K.

*Styles.*—Color—Begonia Rose, Plate I D.

General observations: The new variety most nearly resembles the parent variety "Duc de Rohan," but has leaves of considerably smaller size and a much more sprawly habit of growth, combined with an aged appearance which is especially suitable for use as bonsai type potted plants in patios and in gardens the year round, both without blooms and with blooms in regular season.

I claim:

A new and distinct variety of azalea plant, substantially as herein shown and described, characterized particularly as to novelty by the unique combination of a natural dwarfish habit of growth, with an aged appearance, very small and abundant dark green leaves which fully clothe the plant, profuse, colorful and silky flowers of pink general color tonality and attractive shape, good temperature tolerance, an excellent general attractiveness for bonsai type potted plantings, both with and without blooms and requiring no special care.

No references cited.

T. GRAHAM CRAVER, *Primary Examiner.*

ABRAHAM G. STONE, *Examiner.*